(12) United States Patent (10) Patent No.: US 8,313,427 B2
Ishii (45) Date of Patent: Nov. 20, 2012

(54) ENDOSCOPE AND ENDOSCOPE APPARATUS

(75) Inventor: Hiroshi Ishii, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1161 days.

(21) Appl. No.: 12/174,039

(22) Filed: Jul. 16, 2008

(65) Prior Publication Data

US 2009/0043166 A1 Feb. 12, 2009

(30) Foreign Application Priority Data

Aug. 10, 2007 (JP) ................................. 2007-210005

(51) Int. Cl.
*A61B 1/06* (2006.01)
*A61B 1/00* (2006.01)

(52) U.S. Cl. .......................... 600/170; 600/107; 600/171

(58) Field of Classification Search .................. 600/107, 600/170–171
See application file for complete search history.

(56) References Cited

U.S. PATENT DOCUMENTS

| | | | | |
|---|---|---|---|---|
| 5,140,265 A | * | 8/1992 | Sakiyama et al. | 324/220 |
| 5,325,847 A | | 7/1994 | Matsuno | |
| 5,569,157 A | * | 10/1996 | Nakazawa et al. | 600/107 |
| 5,569,162 A | * | 10/1996 | Komi | 600/130 |
| 5,707,344 A | * | 1/1998 | Nakazawa et al. | 600/127 |
| 5,993,381 A | * | 11/1999 | Ito | 600/131 |
| 6,095,970 A | * | 8/2000 | Hidaka et al. | 600/110 |
| 6,149,598 A | * | 11/2000 | Tanaka | 600/462 |
| 6,361,491 B1 | * | 3/2002 | Hasegawa et al. | 600/175 |
| 6,488,619 B1 | * | 12/2002 | Miyanaga | 600/179 |
| 2007/0118019 A1 | * | 5/2007 | Mitani et al. | 600/176 |

FOREIGN PATENT DOCUMENTS

| | | |
|---|---|---|
| EP | 1 769 719 A1 | 4/2007 |
| JP | 05-199989 A | 8/1993 |
| JP | 08-136829 | 5/1996 |
| JP | 2003-159215 | 6/2003 |
| WO | WO 2004/112594 A1 | 12/2004 |

* cited by examiner

*Primary Examiner* — Philip R Smith
*Assistant Examiner* — Arnaldo Torres Diaz
(74) *Attorney, Agent, or Firm* — Scully, Scott, Murphy & Presser, P.C.

(57) ABSTRACT

An endoscope of the present invention includes a distal end main body portion provided at a distal end portion of an insertion portion, a disposing hole having a first space and a second space that is formed in the distal end main body portion, and an objective lens. The endoscope also includes an image pickup unit that is provided inside disposing hole such that objective lens faces a second opening and that has a shape formed along a part of first space and second space. Image pickup unit is fixed inside disposing hole by a screw that is inserted into distal end main body portion through a screw hole formed in distal end main body portion at an intersecting region between first space and second space.

16 Claims, 10 Drawing Sheets

ENDOSCOPE AND ENDOSCOPE APPARATUS

CROSS REFERENCE TO RELATED APPLICATION

This application claims benefit of Japanese Application No. 2007-210005 filed in Japan on Aug. 10, 2007, the contents of which are incorporated by this reference.

BACKGROUND OF THE INVENTION

1. Field of the Invention

The present invention relates to a side-view endoscope provided with an objective lens that observes a subject in at least one part of the outer peripheral surface of a distal end portion on a distal end side in the insertion direction of an insertion portion, and also to an endoscope apparatus.

2. Description of the Related Art

In recent years, endoscopes have been widely used in the fields of medical treatment and industry. Endoscopes enable observation inside a duct by insertion of an elongated insertion portion into the duct.

Further, an image pickup unit is provided inside a distal end portion on a distal end side in the insertion direction of an insertion portion of an endoscope, for example, an electronic endoscope. The image pickup unit includes a plurality of objective lens groups for observing inside a duct, a solid-state image pickup device such as a CCD, and a member such as an electrical board that exchanges electrical signals with the solid-state image pickup device. The electronic endoscope is arranged so that images of an observation site are picked up by the image pickup unit.

In the case of a direct-view endoscope, in general the image pickup unit is provided inside the distal end portion by first inserting the image pickup unit into a hole portion formed along the insertion direction of the insertion portion at a distal end main body portion provided in the distal end portion, and then fixing the image pickup unit with a screw or the like that is inserted towards the hole portion from the outer peripheral surface side of the distal end portion.

For example, Japanese Patent Application Laid-Open Publication No. 8-136829 discloses a configuration in which an image pickup unit is inserted into an image pickup unit mounting hole portion that is formed along the insertion direction of the insertion portion with respect to a distal end constituting member that corresponds to a distal end main body portion. Further, an objective lens frame that retains an objective lens group including the image pickup unit is fixed by a screw for fixing the image pickup unit. The screw for fixing the image pickup unit is screwed into a screw hole for fixing the image pickup unit that is penetratingly formed from the outer peripheral surface of the distal end portion to the image pickup unit mounting hole. The image pickup unit is thereby fixed inside the image pickup unit mounting hole.

Further, Japanese Patent Application Laid-Open Publication No. 2003-159215 discloses a configuration in which a flange portion that protrudes in an outer peripheral direction is formed at one part of the outer peripheral surface of a fixing ring that retains an objective lens unit including an image pickup unit, and a tapered portion that is oriented in the outer peripheral direction of the distal end portion is formed in the flange portion. When a fixing screw having a tip that is formed in a cone shape via a fixing screw hole is tightened towards the tapered portion from an outer peripheral surface of the distal end portion, the surface at the tip of the fixing screw and the surface of the tapered portion of the objective lens unit come in contact, the fixing ring moves to the rear end side in the insertion direction and contacts against one part of a distal end portion main body provided in the distal end portion. As a result, the image pickup unit is fixed in a hole portion formed along the insertion direction in the distal end portion main body.

SUMMARY OF THE INVENTION

In brief, an endoscope of the present invention is a side-view endoscope in which an objective lens that observes a subject is provided in at least one part of an outer peripheral surface of a distal end portion on a distal end side in an insertion direction of an insertion portion, including: a distal end main body portion provided in the distal end portion of the insertion portion; a disposing hole having a first space that is formed in the distal end main body portion along the insertion direction and that opens as a first opening at a rear end in the insertion direction of the distal end main body portion, and a second space that opens as a second opening in the outer peripheral surface in which the objective lens is provided of the distal end portion and which intersects in a different direction to the insertion direction with the first space; and an image pickup unit that has the objective lens and is provided inside the disposing hole so that the objective lens faces the second opening, and that has a shape formed along a part of the first space and the second space; wherein, at an intersecting region between the first space and the second space, the image pickup unit is fixed inside the disposing hole by a fixing member that is inserted inside the distal end main body portion through an insertion hole formed in the distal end main body portion.

Further, an endoscope apparatus of the present invention is equipped with a side-view endoscope in which an objective lens that observes a subject is provided in at least one part of an outer peripheral surface of a distal end portion on a distal end side in an insertion direction of an insertion portion, the endoscope including: a distal end main body portion provided in the distal end portion of the insertion portion; a disposing hole having a first space that is formed in the distal end main body portion along the insertion direction and that opens as a first opening at a rear end in the insertion direction of the distal end main body portion, and a second space that opens as a second opening in the outer peripheral surface in which the objective lens is provided of the distal end portion and which intersects in a different direction to the insertion direction with the first space; an image pickup unit that has the objective lens and is provided inside the disposing hole so that the objective lens faces the second opening, and that has a shape formed along a part of the first space and the second space; and a fixing member that is inserted into the distal end main body portion through an insertion hole formed in the distal end main body portion and that fixes the image pickup unit inside the disposing hole at an intersecting region between the first space and the second space.

The above and other objects, features and advantages of the invention will become more clearly understood from the following description referring to the accompanying drawings.

DETAILED DESCRIPTION OF THE PREFERRED EMBODIMENTS

Hereunder, embodiments of the present invention are described with reference to the drawings.
(First Embodiment)

Figure 1:
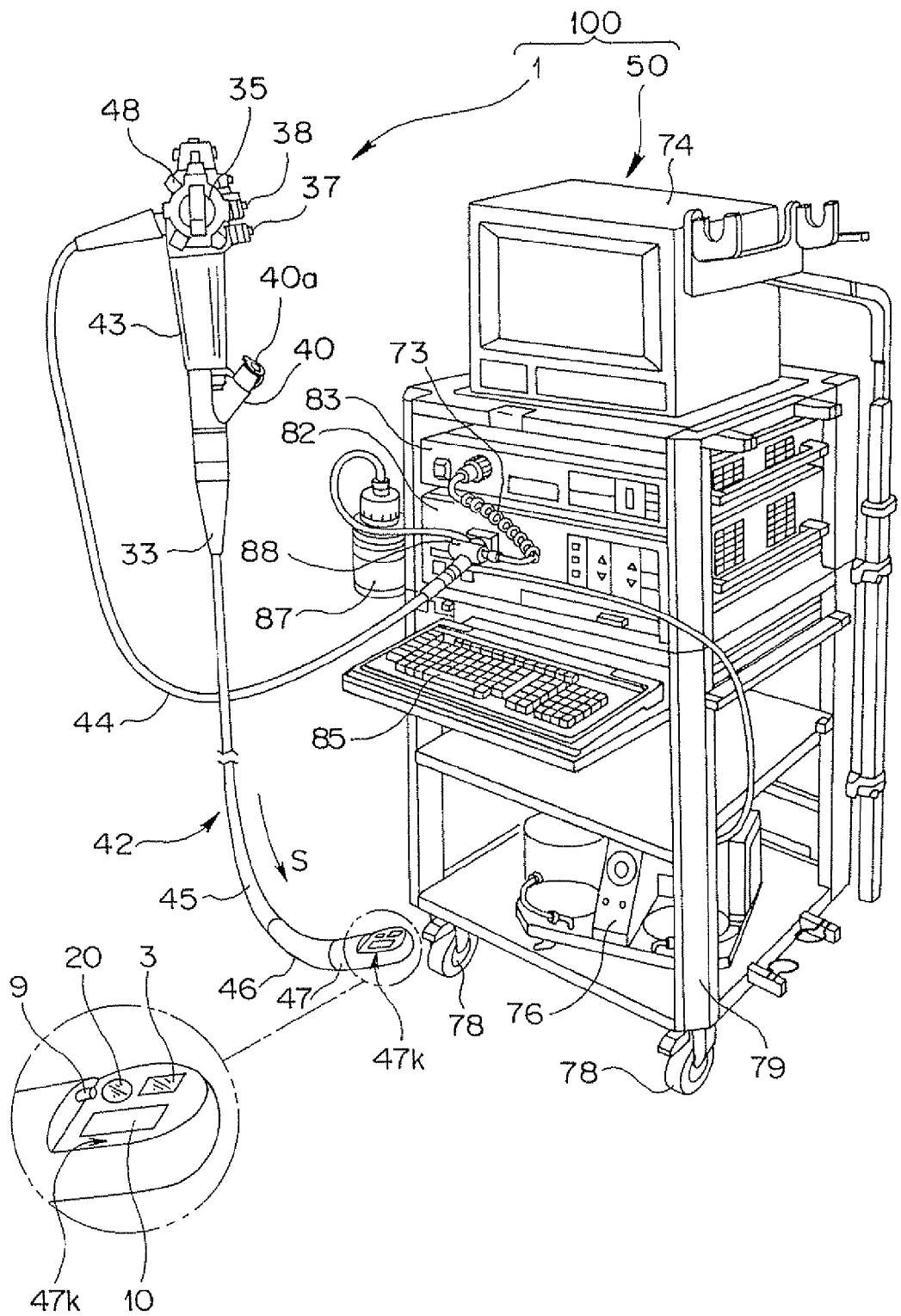
FIG. 1 is an oblique perspective view of the outside of an endoscope apparatus including an endoscope and a peripheral device as viewed diagonally from a front upper right side that illustrates a first embodiment of the present invention.
Figure 2:
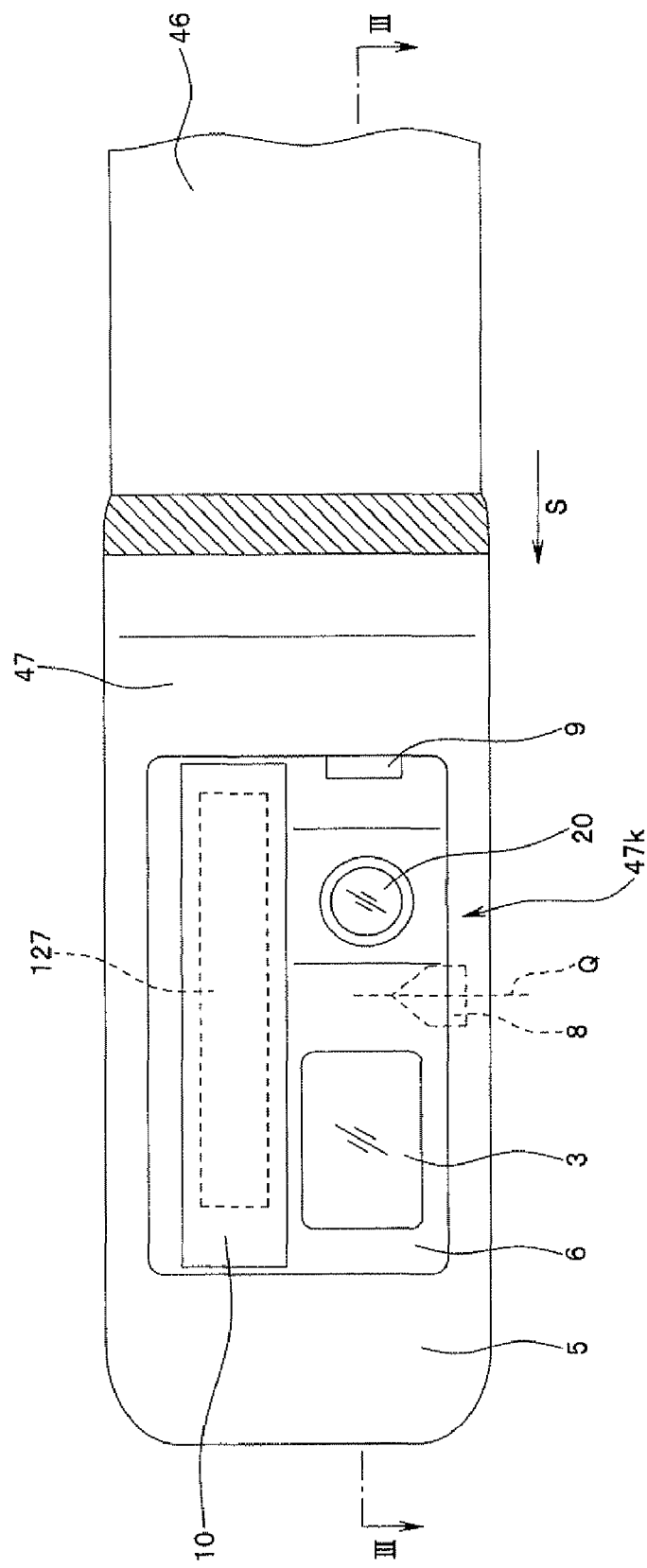
FIG. 2 is a plan view of a distal end side in the insertion direction of an insertion portion of the endoscope illustrated in FIG. 1.
Figure 3:
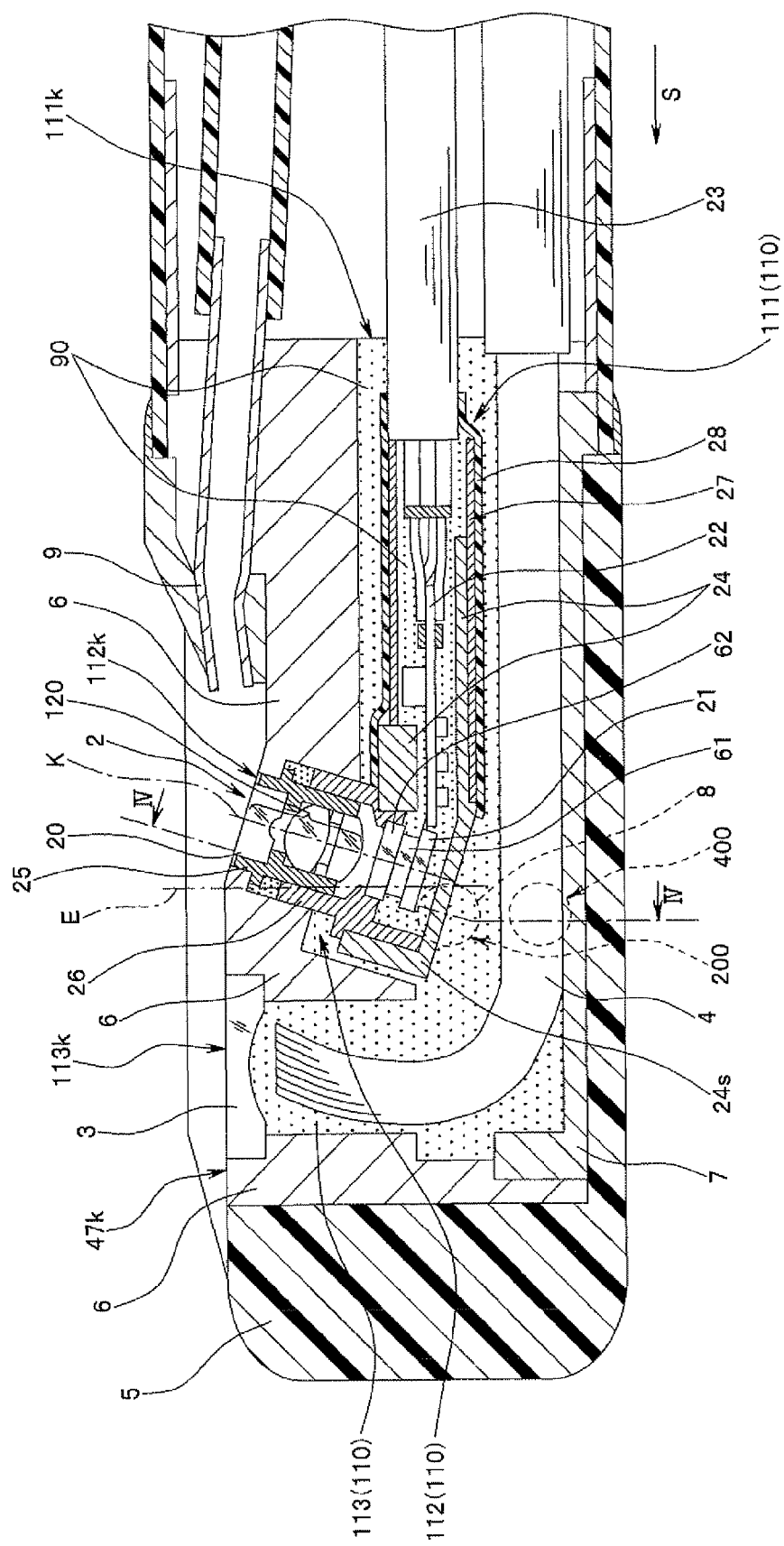
FIG. 3 is a sectional view of the distal end side in the insertion direction of the insertion portion along a line III-III shown in FIG. 2.
Figure 4:
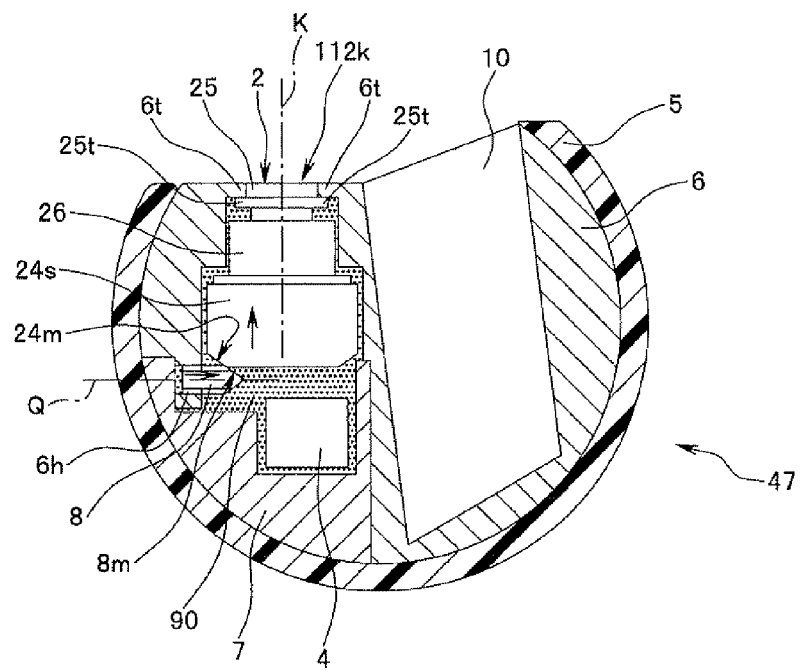
FIG. 4 is a sectional view of a distal end portion of the insertion portion along a line IV-IV shown in FIG. 3.

FIG. 1 is an oblique perspective view of the outside of an endoscope apparatus including an endoscope and a peripheral device as viewed diagonally from a front upper right side that illustrates a first embodiment of the present invention. FIG. 2 is a plan view of a distal end side in the insertion direction of an insertion portion of the endoscope illustrated in FIG. 1. FIG. 3 is a sectional view of the distal end side in the insertion direction of the insertion portion along a line III-III shown in FIG. 2. FIG. 4 is a sectional view of a distal end portion of the insertion portion along a line IV-IV shown in FIG. 3.

As shown in FIG. 1, an endoscope apparatus 100 includes a side-view endoscope 1 and a peripheral device 50. The endoscope 1 includes an operation portion 43, an insertion portion 42, and a universal cord 44 as principal parts. A bend preventing portion 33 that protects the insertion portion 42 is provided at a position linking the insertion portion 42 and the operation portion 43.

The peripheral device 50 includes a light source 82, a video processor 83, a connection cable 73 that electrically connects the light source 82 and the video processor 83, a monitor 74, a keyboard 85, a suction pump 76, and a water supply bottle 87 as principal parts, which are disposed on a rack 79 that has casters 78 mounted at the bottom thereof.

The endoscope 1 and the peripheral device 50 configured in this manner are connected to each other by a connector 88 provided at an end portion of the universal cord 44 that extends from the operation portion 43.

The connector 88 is connected to the light source 82 of the peripheral device 50. An unshown mouthpiece of an air supply/water supply conduit or a suction conduit (neither is illustrated in the figure), an unshown light guide mouthpiece of a light guide 4 described later (see FIG. 3), and electric contact points and the like are provided in the connector 88.

The light guide 4 passes through the inside of the operation portion 43 and the insertion portion 42 of the endoscope 1 from the universal cord 44 and is led as far as to the distal end portion 47, described later, of the insertion portion 42. The light guide 4 supplies an illuminating light from the light source 82 to an illumination lens 3, described later, of the distal end portion 47 to spread and illuminate the inside of a body cavity.

The operation portion 43 of the endoscope 1 is provided with a bending operation knob 35, an air supply/water supply operation button 37, a suction operation button 38, a treatment instrument raiser stand operation knob 48 that executes a raising operation of a treatment instrument raiser stand 127 (see FIG. 2), described later, that is provided so as to face onto a channel opening 10, described later, in the distal end portion 47, and a treatment instrument insertion opening 40 having an opening 40a for inserting a treatment instrument into an unshown treatment instrument insertion channel that also serves as an suction conduit (not shown) provided inside the insertion portion 42 of the endoscope 1.

The insertion portion 42 of the endoscope 1 includes, in order from the distal end side of an insertion direction S, a distal end portion 47, a bending portion 46, and a flexible tube portion 45. The user makes the bending portion 46 perform a bending operation by operating the bending operation knob 35 provided in the operation portion 43. The bending portion 46 is disposed between the distal end portion 47 and the flexible tube portion 45.

At one part of the outer peripheral surface of the distal end portion 47 is formed a concave notch portion 47k that is notched into one outer peripheral surface side. As shown in FIG. 1 and FIG. 2, a channel opening 10 that is an opening of the distal end portion of the treatment instrument insertion channel is provided in one outer peripheral surface of the notch portion 47k.

As shown in FIG. 1 and FIG. 2, in the vicinity of the channel opening 10 at one outer peripheral surface of the notch portion 47k are provided an objective lens 20 and an illumination lens 3 that constitute an image pickup unit 2, described later, which is provided in the distal end portion 47.

Further, as shown in FIG. 1 and FIG. 2, an air supply/water supply nozzle 9 is provided protrudingly so as to face the objective lens 20 in a wall surface on the rear end side in the insertion direction S of the notch portion 47k of the distal end portion 47. When the user operates the air supply/water supply operation button 37 of the operation portion 43, the nozzle 9 sprays a fluid such as water or air at the outer surface of the objective lens 20 to remove dirt from the lens surface of the objective lens 20.

Furthermore, as shown in FIG. 2, inside the channel opening 10 of the distal end portion 47 is disposed an unshown treatment instrument raiser stand 127 that raises a treatment instrument such as a catheter or a guidewire or the like (neither is shown in the figure).

Upon a user performing an operation to rotate the operation knob 48, the treatment instrument raiser stand 127 changes the travelling direction of a guidewire or a treatment instrument or the like that is inserted into the treatment instrument insertion channel from the opening 40a of the treatment instrument insertion opening 40 from a travelling direction inside the treatment instrument insertion channel along the insertion direction S to the direction of the channel opening 10.

Next, an outline of the configuration inside the distal end portion 47 of the endoscope 1 is described using FIG. 3 and FIG. 4.

As shown in FIG. 3, a distal end main body portion 6 is provided in the distal end portion 47. A distal end cover 5 is provided at the distal end in the insertion direction S and the outer circumference of the distal end main body portion 6 excluding the notch portion 47k. The distal end cover 5 is made of a non-conductive member such as resin and arranged so as to cover the outer circumference in question and the distal end. The distal end cover 5 is fixed with adhesive or the like to the distal end main body portion 6.

An image pickup unit disposing hole 110 in which the image pickup unit 2 is provided is formed in the distal end main body portion 6. More specifically, in the image pickup unit disposing hole 110, a bottom portion (lower part in FIG. 3) facing the notch portion 47k is open, and a rear end side in the insertion direction S has a first space 111 formed along the insertion direction S that opens as a first opening 111k.

The image pickup unit disposing hole 10 has a second space 112 that opens as a second opening 112k in the notch portion 47k of the distal end portion 47. The second space 112 is formed so as to intersect with a distal end side in the insertion direction S of the first space 111 along a different direction to the insertion direction S, more specifically, along the direction of an axis K that inclines towards a diagonally rearward side in the insertion direction S at a predetermined angle from an axis E that is perpendicular to the insertion direction S.

The image pickup unit disposing hole 110 also has a third space 113 that opens as a third opening 113k in the notch portion 47k of the distal end portion 47. The third space 113 is formed so as to intersect with the distal end side in the insertion direction S along the axis E that is perpendicular to the insertion direction S at a position that is further on the distal end side than a position at which the second space 112 intersects in the first space 111.

The image pickup unit 2 that has a shape formed along the upper side in FIG. 3 of the first space 111 and the second space is provided in one part of the first space 111, more specifically, on the upper side in FIG. 3 of the first space 111, and in the second space.

The principal parts of the image pickup unit 2 include a plurality of objective lens groups 120 that have an objective lens 20, an objective lens frame 25 that retains the plurality of objective lens groups 120, an image pickup device 21, a device frame 26 that retains the image pickup device 21, an image pickup unit retaining frame 24 that retains the device frame 26, an electrical board 22, a shielding material 27, a heat-shrinkable tube 28, and a thermoplastic resin 90.

The objective lens frame 25 is arranged inside the second space 112 such that the objective lens 20 is positioned facing the second opening 112k along the axis K. The inner circumference of the top surface side (hereunder, referred to simply as "top surface side") that is the second opening 112k side of the device frame 26 is fitted along the axis K on the outer circumference of the bottom side (hereunder, referred to simply as "bottom side") facing the second opening 112k of the objective lens frame 25.

The image pickup device 21 is arranged so as to be positioned on the axis K at an image-formation position of the objective lens group 120, at the bottom side of the objective lens group 120. A first cover glass 61 that protects an image pickup surface is adhered to the image pickup surface that is the top surface of the image pickup device 21. A second cover glass 62 is adhered to the top surface of the first cover glass 61. The outer circumference of the second cover glass 62 is fixed in the inner circumference of the device frame 26 at a midway position along the axis K of the device frame 26. As a result, the image pickup device 21 is retained by the device frame 26.

A site 24s on the distal end side in the insertion direction S that has a shape that inclines diagonally upward at the distal end side in the insertion direction S as shown in FIG. 3, in the image pickup unit retaining frame 24 having a shape formed along the insertion direction S on the upper side in FIG. 3 of the first space 111, is fitted to the bottom of the device frame 26 and one part of the outer circumference of the bottom.

Further, at a region where the first space 111 and the second space 112 intersect, more specifically, in the present embodiment, at a site of the distal end main body portion 6 facing a region 200 on the bottom side of the distal end site 24s in the image pickup unit retaining frame 24, as shown in FIG. 4, a screw hole 6h that is an insertion hole that passes through the distal end main body portion 6 is formed so as to face the bottom of the distal end site 24s along an axis Q that is perpendicular to the axis E and the insertion direction S.

A screw 8 that is a fixing member that fixes the image pickup unit 2 is screwed into the screw hole 6h such that the tip thereof contacts against the bottom of the distal end site 24s. In this connection, the region 200 is a region which, for example, when the bending portion 46 is bent, is most agitated in the image pickup unit 2 and to which a force that pushes and pulls in the insertion direction S is most applied by the signal cable 23.

The screw 8 is a screw without a head, and has a tip that is formed in a cone shape. Hence, as shown in FIG. 4, a first inclined portion 8m that is oriented towards the second opening 112k side is formed at the tip of the screw 8. Further, a second inclined portion 24m having a face abutting against a face of the first inclined portion 8m is formed at a site against which the first inclined portion 8m of the screw 8 contacts in the distal end site 24s of the image pickup unit retaining frame 24.

As shown in FIG. 4, when the screw 8 is screwed into the screw hole 6h so that a face of the first inclined portion 8m abuts against a face of the second inclined portion 24m, the force that screws in the screw 8 along the axis Q is converted into a force that pushes up the distal end site 24s to the second opening 112k side along the axis K by the abutting of the faces of the second inclined portion 24m and the first inclined portion 8m that is oriented to the second opening 112k side.

As a result, because the distal end site 24s is pushed up to the second opening 112k side, the device frame 26 in which the distal end site 24s is fitted is pushed up to the second opening 112k side and the objective lens frame 25 fitted in the device frame 26 is also pushed up to the second opening 112k side. Further, a flange portion 25t formed in the outer circumference of the objective lens frame 25 contacts against a positioning site 6t of the distal end main body portion 6 that is positioned on the second opening 112k side in the second space 112, to thereby fix the image pickup unit 2 inside the image pickup unit disposing hole 110.

Returning to FIG. 3, the distal end side in the insertion direction S of the electrical board 22 is electrically connected to the image pickup device 21. A plurality of electronic components such as a capacitor, a resistor, and a transistor that carry out the exchange of electrical signals with the image pickup device 21 are mounted on the electrical board 22.

The electrical board 22 is provided along the insertion direction S in the first space 111. A lead wire that extends from the distal end in the insertion direction S of the signal cable 23 that passes through the inside of the connector 88, the universal cord 44, the operation portion 43, and the insertion portion 42 via the connection cable 73 from the video processor 83 is electrically connected to the rear end side in the insertion direction S of the electrical board 22.

In the first space 111, a distal end side in the insertion direction S of the heat-shrinkable tube 28 that extends along the insertion direction S is connected via the shielding material 27 in the inner circumference direction to the outer circumference of a site in the insertion direction S of the image pickup unit retaining frame 24. The rear end side in the insertion direction S of the heat-shrinkable tube 28 is connected to the distal end side in the insertion direction S of the signal cable 23.

The electrical board 22 is disposed so as to extend inside a space covered by the heat-shrinkable tube 28. In the image pickup unit 2, the thermoplastic resin 90 is filled inside a space covered by the image pickup unit retaining frame 24 and the heat-shrinkable tube 28.

The light guide 4 is passed through the first space 111 at a position that is further on the bottom side than the image pickup unit 2. The distal end side of the light guide 4 that is passed through the inside of the first space 111 passes through the inside of the third space 113 and arranged at a position facing the illumination lens 3 that is provided so as to face the opening 113k in the notch portion 47k of the third space 113.

Further, in the first space 111 to third space 113, a light guide cover 7 is provided at the bottom of the light guide 4 along the insertion direction S. The light guide cover 7 retains the light guide 4 and also blocks an opening in the bottom side of the distal end main body portion 6. The light guide cover 7 maintains the inner area between the first space 111 and the third space 113 in a watertight condition and, as shown in FIG. 4, also maintains the screw hole 6h in a watertight condition after the screw 8 is screwed therein by covering the screw hole 6h. The thermoplastic resin 90 is also filled inside the area from the first space 111 to third space 113 that is covered in a watertight condition by the light guide cover 7.

Next, a method of assembling the distal end portion 47 configured in this manner is briefly described.

First, with respect to the upper side of the first space 111 and the second space 112, the image pickup unit 2 is disposed along the spaces 111 and 112 from the opening on the bottom of the distal end main body portion 6. Next, after disposing the light guide 4 at a position further on the bottom side than the image pickup unit 2 of the first space 111 and in the third space 113, the thermoplastic resin 90 is filled in the area from the first space 111 to the third space 113.

Subsequently, when the screw 8 is screwed into the screw hole 6h of the distal end main body portion 6 such that a face of the first inclined portion 8m at the tip of the screw 8 abuts against a face of the second inclined portion 24m formed at the bottom of the distal end site 24s of the image pickup unit retaining frame 24, the force that screws in the screw 8 along the axis Q is converted into a force that pushes up the distal end site 24s to the second opening 112k side along the axis K.

As a result, because the distal end site 24s is pushed up to the second opening 112k side, the device frame 26 in which the distal end site 24s is fitted is pushed up to the second opening 112k side and the objective lens frame 25 fitted in the device frame 26 is also pushed up to the second opening 112k side. Further, the flange portion 25t formed in the outer circumference of the objective lens frame 25 contacts against the positioning site 6t that is positioned on the second opening 112k side in the second space 112 to thereby fix the image pickup unit 2 inside the image pickup unit disposing hole 110.

Finally, after making the inner area from the first space 111 to the third space 113 and the screw hole 6h watertight by covering the opening of the bottom of the distal end main body portion 6 with the light guide cover 7, the distal end portion 47 is assembled by adherently fixing the distal end cover 5 onto the outer circumference excluding the notch portion 47k of the distal end main body portion 6 and the outer circumference of the light guide cover 7.

Next, the working method for detaching the image pickup unit 2 from the image pickup unit disposing hole 110 of the distal end main body portion 6 when replacing the image pickup unit 2 is described.

First, the distal end cover 5 is removed, followed by removal of the light guide cover 7. Thereafter, the thermoplastic resin 90 is removed. Next, the light guide 4 is withdrawn to outside of the distal end main body portion 6 from the opening on the bottom surface side of the distal end main body portion 6. As a result, the image pickup unit 2 is exposed with respect to the opening on the bottom surface side of the distal end main body portion 6.

Finally, the screw 8 is removed from the screw hole 6h and the image pickup unit 2 is removed to outside of the distal end main body portion 6 from the opening in the bottom surface side of the distal end main body portion 6. Thus, the image pickup unit 2 is removed from the image pickup unit disposing hole 110 of the distal end main body portion 6.

Thus, according to the present embodiment a configuration is described in which, after the image pickup unit 2 is disposed in the upper side of the first space 111 and the second space 112 of the image pickup unit disposing hole 110, in a region 200 in the image pickup unit 2 where the first space 111 and the second space 112 intersect is the most agitated and is the region to which a force that pushes and pulls in the insertion direction S is imparted most by the signal cable 23 when, for example, the bending portion 46 is bent that is at the bottom side of the distal end site 24s of the image pickup unit retaining frame 24 located in the second space 112, by screwing the screw 8 into the screw hole 6h at the region 200 such that a face of the first inclined portion 8m at the tip of the screw 8 abuts against a face of the second inclined portion 24m of the distal end site 24s, the distal end site 24s is pushed up to the second opening 112k side and the flange portion 25t of the objective lens frame 25 is caused to contact against the positioning site 6t of the distal end main body portion 6 to thereby fix the image pickup unit 2 inside the image pickup unit disposing hole 110.

Further, it is described that after the image pickup unit 2 is exposed with respect to the opening of the bottom of the distal end main body portion 6, by merely removing the screw 8 from the screw hole 6h, the image pickup unit 2 can be removed from the image pickup unit disposing hole 110.

According to this configuration, replacement of the image pickup unit 2 can be easily performed using the screw 8 in comparison to the conventional configuration in which the image pickup unit 2 is fixed in the image pickup unit disposing hole 110 using only an adhesive.

Further, in the region 200 where the first space 111 and the second space 112 intersect, which is most agitated with respect to the image pickup unit 2, for example, when the bending portion 46 is bent and which is most subject to a force that pushes and pulls in the insertion direction S that is imparted by the signal cable 23, since the image pickup unit 2 is fixed with the screw 8 at the region 200, even if the image pickup unit 2 is agitated or is subjected to a force in the insertion direction S, it is possible to prevent detachment of the members included in the image pickup unit 2, for example, detachment of the electrical board 22 from the image pickup device 21. It is thus possible to provide the side-view endoscope 1 that has a configuration that improves the durability of the image pickup unit 2.

Furthermore, the present embodiment has a configuration in which the screw 8 is screwed into the screw hole 6h at an intersecting region 200 located on the bottom side of the distal end site 24s of the image pickup unit retaining frame 24, to thereby fix the image pickup unit 2 in the image pickup unit disposing hole 110. It is therefore possible to definitely secure space to provide the screw 8 in the distal end portion 47 even if the diameter of the distal end portion 47 is reduced and the objective lens group 120 is, for example, made more compact in a direction along the axis K.

(Second Embodiment)

Figure 5:
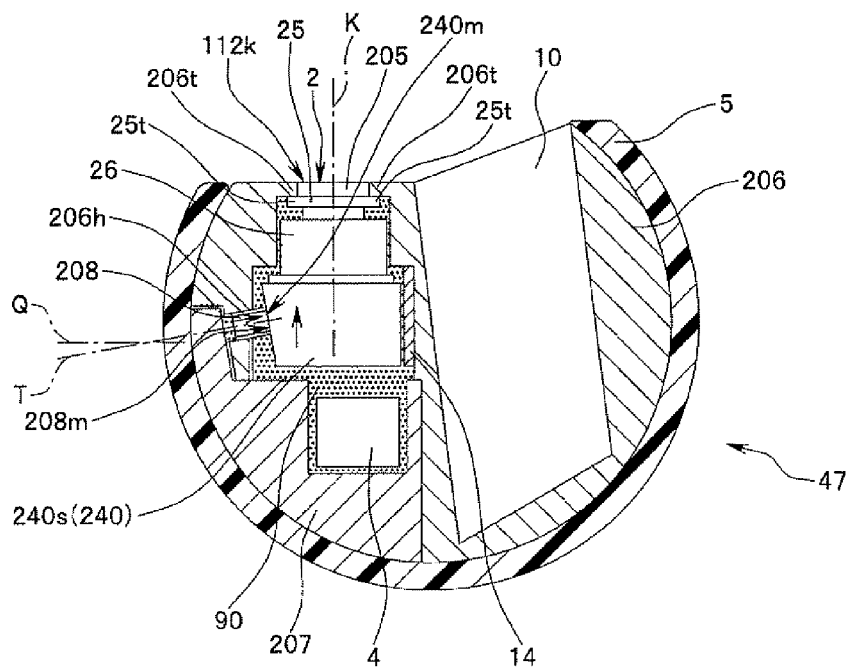
FIG. 5 is a sectional view of a distal end portion of an insertion portion of an endoscope that illustrates a second embodiment.

FIG. 5 is a sectional view of a distal end portion of an insertion portion of an endoscope illustrating a second embodiment of the present invention.

In comparison to the endoscope of the first embodiment illustrated in FIG. 1 to FIG. 4 described above, the configuration of the endoscope of the second embodiment differs with respect to the shape of the tip side of the screw and the formation direction of the screw hole with respect to the distal end main body portion. Hence, only these differences are described below, and the same reference numerals are assigned to constituent parts that are the same as the first embodiment and a description of those parts is omitted.

As shown in FIG. 5, a site 240s on the distal end side in the insertion direction S that has a shape that inclines diagonally upward at the distal end side in the insertion direction S as shown in FIG. 3, in an image pickup unit retaining frame 240 having a shape formed along the insertion direction S on the upper side in FIG. 3 of the first space 111, is fitted to the bottom of the device frame 26 and one part of the outer circumference of the bottom.

Further, at a region where the first space 111 and the second space 112 intersect, more specifically, in the present embodiment, at a site of a distal end main body portion 206 facing the region 200 on the bottom side of the distal end site 240s in the image pickup unit retaining frame 240, as shown in FIG. 5, a screw hole 206h that is an insertion hole that passes through the distal end main body portion 206 is formed so as to face the side surface of the distal end site 240s along an axis T that inclines at a set angle to the second opening 112k side with respect to the axis Q that is perpendicular to the axis E and the insertion direction S. A screw 208 that is a fixing member that fixes the image pickup unit 2 is screwed into the screw hole 206h such that the tip thereof contacts against a side surface of the distal end site 240s.

The screw 208 is a screw without a head, and has a tip that is formed in a flat face 208m. Further, a third inclined portion 240m having a face abutting against the flat face 208m is formed at a site against which the flat face 208m of the screw 208 contacts in the distal end site 240s of the image pickup unit retaining frame 240.

An elastic member 14 may be provided in a space between the distal end main body portion 206 and a side surface on an opposite side to the side surface against which the flat face 208m of the screw 208 contacts at the distal end site 240s. In this connection, the elastic member 14 is provided by fixing one side surface of the elastic member 14 to the distal end main body portion 206.

As shown in FIG. 5, when the screw 208 is screwed into the screw hole 206h such that the flat face 208m abuts against a face of the third inclined portion 240m, the force that screws in the screw 208 along the axis T is converted into a force that pushes up the distal end site 240s to the second opening 112k side along the axis K by the abutting of the flat face 208m against the face of the third inclined portion 240m.

At this time, if the elastic member 14 is provided, when the screw 208 is screwed in along the axis T, a side surface on an opposite side to the side surface against which the flat face 208m of the screw 208 contacts in the distal end site 240s contacts against the elastic member 14. It is therefore possible to efficiently convert the force that screws in the screw 208 into a force that pushes up the distal end site 240s to the second opening 112k side along the axis K without pressing the distal end site 240s excessively along the axis T.

As a result, because the distal end site 240s is pushed up to the second opening 112k side, the device frame 26 in which the distal end site 240s is fitted is pushed up to the second opening 112k side and the objective lens frame 25 fitted in the device frame 26 is also pushed up to the second opening 112k side. Further, the flange portion 25t formed in the outer circumference of the objective lens frame 25 contacts against a positioning site 206t of the distal end main body portion 206 that is located on the second opening 112k side in the second space 112, to thereby fix the image pickup unit 2 inside the image pickup unit disposing hole 110.

Furthermore, in the first space 111 to third space 113, a light guide cover 207 is provided at the bottom of the light guide 4 along the insertion direction S. The light guide cover 207 retains the light guide 4 and also blocks an opening of the bottom side of the distal end main body portion 206. The light guide cover 207 maintains the inner area between the first space 111 and the third space 113 in a watertight condition and, as shown in FIG. 5, also maintains the screw hole 206h in a watertight condition after the screw 208 is screwed therein by covering the screw hole 206h.

The remaining configuration and actions of the distal end portion 47 are the same as in the above described first embodiment. Similar advantages as those of the above described first embodiment can also be obtained by the above-described configuration.

According to the present embodiment, a configuration is described in which the elastic member 14 is provided between the distal end main body portion 206 and a side surface on an opposite side to the side surface against which the flat face 208m of the screw 208 contacts at the distal end site 240s. However, similar advantages as those of the above described first embodiment can be obtained according to the present embodiment even if the elastic member 14 is not provided in consideration of the fact that excessive pressing of the distal end site 240s along the axis T by the screw 208 is prevented by the flexible thermoplastic resin 90 that is filled in the distal end portion 47.

(Third Embodiment)

Figure 6:
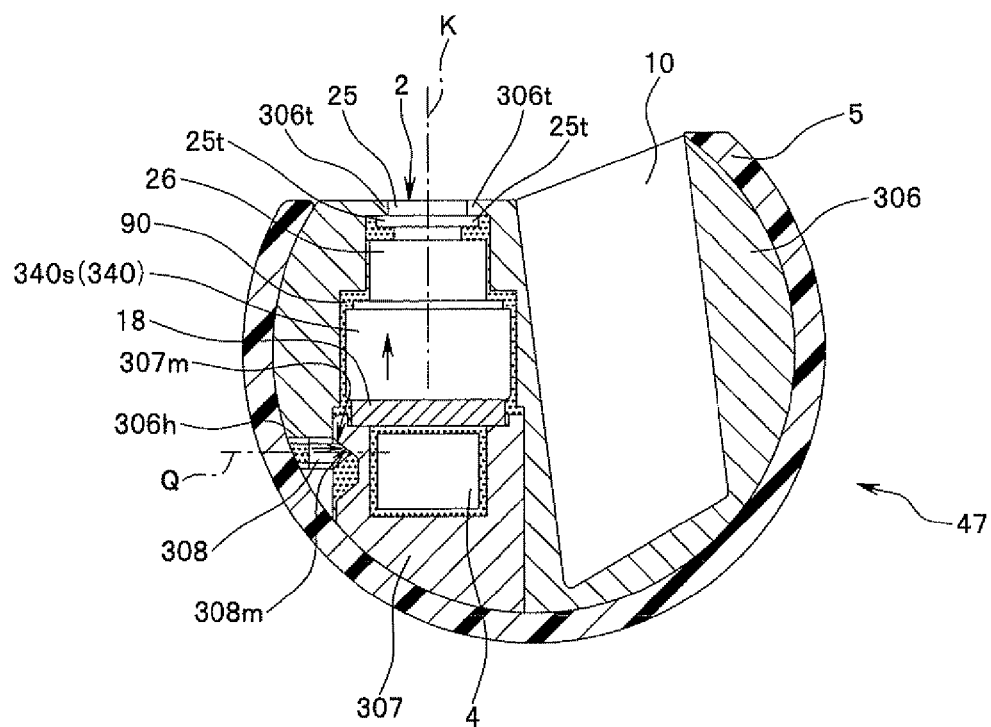
FIG. 6 is a sectional view of a distal end portion of an insertion portion of an endoscope that illustrates a third embodiment.
Figure 7:
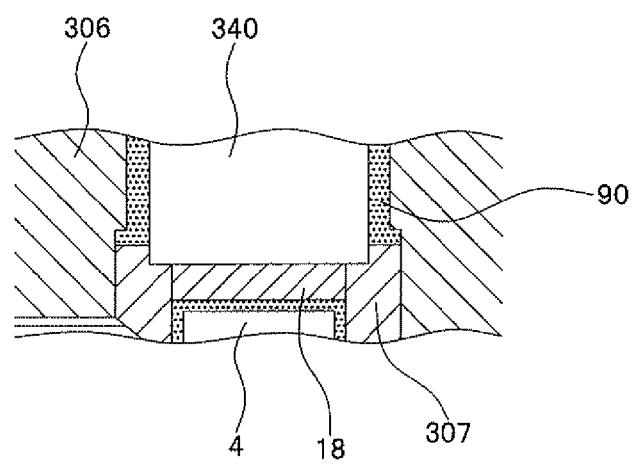
FIG. 7 is a partial sectional view that illustrates a modification example in which a portion of a light guide cover shown in FIG. 6 is in direct contact with a distal end site of an image pickup unit retaining frame.

FIG. 6 is a sectional view of a distal end portion of an insertion portion of an endoscope that illustrates a third embodiment of the present invention. FIG. 7 is a partial sectional view that illustrates a modification example in which a part of a light guide cover shown in FIG. 6 is in direct contact with a distal end site of an image pickup unit retaining frame.

In comparison with the endoscope of the first embodiment illustrated in FIG. 1 to FIG. 4 described above the configuration of the endoscope of the third embodiment differs in the respect that at the aforementioned intersecting region, instead of the image pickup unit retaining frame, the image pickup unit is fixed by pushing up the light guide cover by means of a screw. Hence, only this difference is described below and the same reference numerals are assigned to constituent parts that are the same as in the first embodiment, and a description of those parts is omitted.

As shown in FIG. 6, a site 340s on the distal end side in the insertion direction S that has a shape that inclines diagonally upward at the distal end side in the insertion direction S as shown in FIG. 3, in an image pickup unit retaining frame 340 having a shape formed along the insertion direction S on the upper side in FIG. 3 of the first space 111, is fitted to the bottom of the device frame 26 and one part of the outer circumference of the bottom.

In the area from the first space 111 to the third space 113, a light guide cover 307 is provided at the bottom of the light guide 4 along the insertion direction S. The light guide cover 307 retains the light guide 4 and also blocks an opening of the bottom side of a distal end main body portion 306. The light guide cover 307 maintains the inner area between the first space 111 and the third space 113 in a watertight condition.

Further, between the light guide 4 that is retained by the light guide cover 307 and the distal end site 340s, an elastic member 18 is provided in a condition in which the elastic member 18 contacts against the bottom of the distal end site 340s by mounting the elastic member 18 on one part of the top surface of the light guide cover 307.

Furthermore, at a region where the first space 111 and the second space 112 intersect, more specifically, in the present embodiment, at a site that is further on the bottom surface side in FIG. 3 than the above described intersecting region 200 of the first embodiment and second embodiment, more specifically, at a site of the distal end main body portion 306 facing a region 400 (see FIG. 3) at a site of the bottom surface side of the light guide cover 307, as shown in FIG. 6, a screw hole 306h that is an insertion hole that passes through the distal end main body portion 306 is formed so as to face the side surface of the light guide cover 307 along the axis Q that is perpendicular to the axis E and the insertion direction S. A screw 308 that is a fixing member that fixes the image pickup unit 2 is screwed into the screw hole 306h such that the tip thereof contacts against the side surface of the light guide cover 307.

The screw 308 is a screw without a head, and has a tip formed in a conical shape. Hence, as shown in FIG. 6, a fourth inclined portion 308m that is oriented towards the second opening 112k side is formed at the tip of the screw 308. Further, a fifth inclined portion 307m having a face abutting against a face of the fourth inclined portion 308m is formed at a site against which the fourth inclined portion 308m of the screw 308 contacts at the side surface of the light guide cover 7.

As shown in FIG. 6, when the screw 308 is screwed into the screw hole 306h such that a face of the fourth inclined portion 308m abuts against a face of the fifth inclined portion 307m, a force that screws in the screw 308 along the axis Q is converted into a force that pushes up the light guide cover 307 to the second opening 112k side along the axis K by the abutting of the faces of the fifth inclined portion 307m and the fourth inclined portion 308m that is oriented to the second opening 112k side.

As a result, because the light guide cover 307 is pushed up to the second opening 112k side, the elastic member 18 is pushed up to the second opening 112k side and the distal end site 340s is pushed up to the second opening 112k side. Thereby, the device frame 26 in which the distal end site 340s is fitted is pushed up to the second opening 112k side. Further, the objective lens frame 25 that is fitted in the device frame 26 is also pushed up to the second opening 112k side, and the flange portion 25t formed in the outer circumference of the objective lens frame 25 contacts against a positioning site 306t of the distal end main body portion 306 that is located on the second opening 112k side in the second space 112 to thereby fix the image pickup unit 2 in the image pickup unit disposing hole 110.

At this time, because the elastic member 18 is provided between the distal end site 340s and the light guide cover 307, it is possible to prevent the rigid light guide cover 307 from directly pushing up the distal end site 340s to the second opening side and damaging the distal end site 340s.

The remaining configuration and actions of the distal end portion 47 are the same as in the above described first embodiment. Similar advantages as those of the above described first embodiment can also be obtained by the above-described configuration.

According to the present embodiment, a configuration is described in which the elastic member 18 is provided between the distal end site 340s and the light guide cover 307, and by screwing the screw 308 into the screw hole 306h, the light guide cover 307 pushes up the distal end site 340s onto the second opening 112k side via the elastic member 18. However, the present embodiment is not limited thereto, and as shown in FIG. 7, a configuration may be adopted in which one part of the light guide cover 307 directly pushes up the distal end site 340s onto the second opening 112k side.

Further, in the above described first to third embodiments, the objective lens group 120 and the image pickup device 21 are provided along the axis K in the second space 112. That is, the objective lens 20 is disposed in a condition in which the objective lens 20 inclines diagonally towards the rearward side in the insertion direction S with respect to the axis E that is perpendicular to the insertion direction S.

However, the present invention is not limited thereto, and similar advantages as those of the first to third embodiments described above can be obtained even when, with respect to the distal end main body portion, the second space 112 is formed along the axis E that is perpendicular to the insertion direction S, and the objective lens group 120 and the image pickup device 21 are provided along the axis E.

In this connection, although even in a conventional direct-view endoscope an image pickup unit has been fixed with a screw or the like inside an image pickup unit disposing hole in a distal end portion, when the diameter of the distal end portion is made thinner, the space in which to provide the screw around the image pickup unit of the distal end portion is lost. Therefore, the image pickup unit is fixed inside the image pickup unit disposing hole with an adhesive.

However, when the image pickup unit is fixed using an adhesive, there is the problem that time is required to adherently fix the image pickup unit and the working efficiency declines. Further, the reparability is poor when replacing the image pickup unit.

Therefore, even for direct-view endoscopes, there has been a desire for a configuration that enables an image pickup unit to be fixed with a screw even when attempting to decrease the diameter of the distal end portion.

Figure 8:
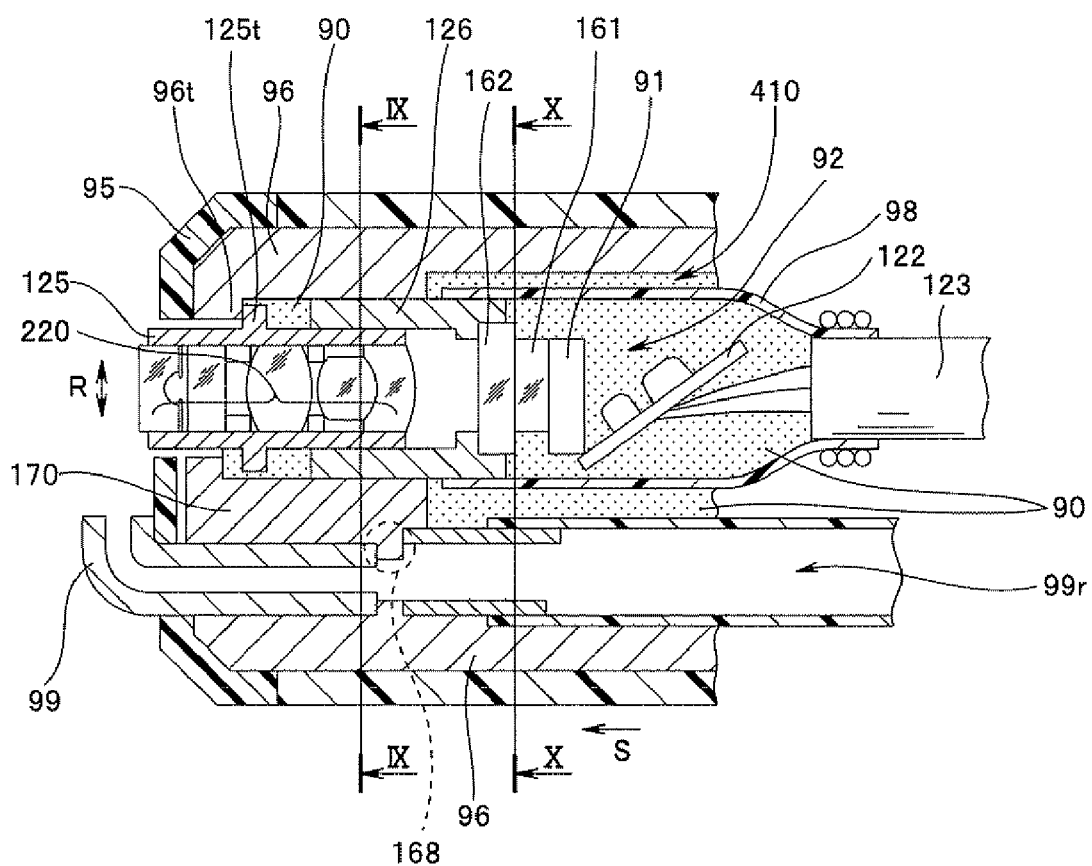
FIG. 8 is a partial sectional view illustrating a distal end side of an insertion portion of a direct-view endoscope.
Figure 9:
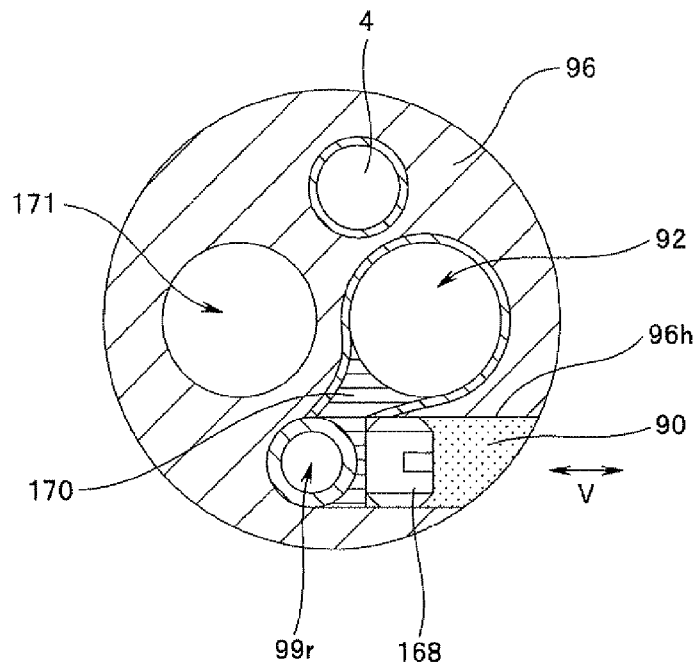
FIG. 9 is a sectional view of the distal end portion along a line IX-IX shown in FIG. 8.
Figure 10:
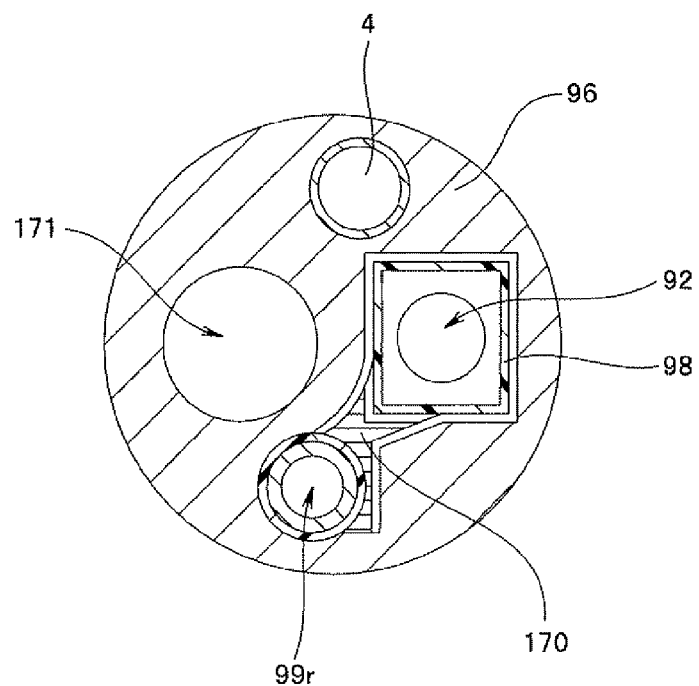
FIG. 10 is a sectional view of the distal end portion along a line X-X shown in FIG. 8.

Hereunder, a configuration in which an image pickup unit can be fixed with a screw even when attempting to decrease the diameter of the distal end portion in a direct-view endoscope is described referring to FIG. 8 to FIG. 10. FIG. 8 is a partial sectional view illustrating a distal end side of an insertion portion of a direct-view endoscope. FIG. 9 is a sectional view of the distal end portion along a line IX-IX shown in FIG. 8. FIG. 10 is a sectional view of the distal end portion along a line X-X shown in FIG. 8.

As shown in FIG. 8, a distal end main body portion 96 is provided at a distal end portion of the insertion portion of a direct-view endoscope. The distal end main body portion 96 is covered by a distal end cover 95 on the outer circumference thereof and on a surface at a distal end in the insertion direction S (hereunder, referred to simply as "distal end"). In the distal end main body portion 96; an image pickup unit 92 is disposed in an image pickup unit disposing hole 410 formed along the insertion direction S. The image pickup unit 92 includes an objective lens group 220, an image pickup device 91, an electrical board 122, and a heat-shrinkable tube 98 as principal parts.

More specifically, the objective lens group 220 that is retained by an objective lens frame 125 is retained at the distal end side of the image pickup unit disposing hole 410, and the inner circumference of the distal end side of a device frame 126 is fitted on the outer circumference of the side of the rear end in the insertion direction S (hereunder, referred to simply as "rear end") of the objective lens frame 125. The objective lens frame 125 is positioned by means of contact of a protruding portion 125*t* against a positioning portion 96*t* of the distal end main body portion 96.

Further, the image pickup device 91 is provided at an image-formation position located toward the rear in the insertion direction S (hereunder, referred to simply as "rearward") of the objective lens groups 220. A first cover glass 161 is adherently attached to the image pickup surface of the image pickup device 91. A second cover glass 162 is adherently attached to a distal end face of the first cover glass 161. The outer circumference of the second cover glass 162 is fitted in the inner circumference at the rear end of the device frame 126.

The electrical board 122 is electrically connected to the image pickup device 91. A lead wire of the distal end side of a signal cable 123 that passes from an unshown video processor through the inside of an endoscope connector, a universal cord, an operation portion, and an insertion portion (none of these are illustrated in the figures) is electrically connected to the electrical board 122.

The distal end of the heat-shrinkable tube 98 is fixed on the outer circumference of the rear end of the device frame 126. The rear end of the heat-shrinkable tube 98 is fixed on the outer circumference of the distal end side of the signal cable 123. The thermoplastic resin 90 is filled inside a space that is hermetically sealed by the heat-shrinkable tube 98, together with the electrical board 122 and the image pickup device 91. The thermoplastic resin 90 is also filled in a space between the image pickup unit 92 and the image pickup unit disposing hole 410.

Along the insertion direction S in the distal end main body portion 96, in addition to the image pickup unit disposing hole 410 are provided a hole in which a treatment instrument insertion channel 171 is arranged and a hole in which the light guide 4 is arranged.

As shown in FIG. 8 to FIG. 10, an air supply/water supply nozzle 99 is disposed in the image pickup unit disposing hole 410 in addition to the image pickup unit 92. The air supply/water supply nozzle 99 has a channel 99*r* via an interposing member 170 with respect to the image pickup unit 92.

The interposing member 170 is adherently fixed to the image pickup unit 92, and is provided such that the interposing member 170 is not adhered to the air supply/water supply nozzle 99.

A screw hole 96*h* is formed in a direction V that is perpendicular to a width direction R of the objective lens group 220 and the insertion direction S at a position facing the air supply/water supply nozzle 99 of the distal end main body portion 96. A screw 168 is screwed into the screw hole 96*h* such that the tip of the screw 168 contacts against a site of the interposing member 170 positioned around the air supply/water supply nozzle 99.

As a result, the air supply/water supply nozzle 99 is fixed in the image pickup unit disposing hole 410 via the interposing member 170 by means of the screw 168, and the image pickup unit 92 that is adhered to the interposing member 170 is also fixed in the image pickup unit disposing hole 410 via the interposing member 170 by the screw 168.

Next, the method of fixing the image pickup unit 92 and the air supply/water supply nozzle 99 in the image pickup unit disposing hole 410 of the distal end main body portion 96 configured in this manner is described.

First, the air supply/water supply nozzle 99 is inserted into the image pickup unit disposing hole 410 from the rearward side in the insertion direction S. Thereafter, at the same time as inserting the image pickup unit 92 into the image pickup unit disposing hole 410 from the rearward side in the insertion direction S, the interposing member 170 is inserted into the image pickup unit disposing hole 410 from the rearward side in the insertion direction S with the image pickup unit 92. The thermoplastic resin 90 is also filled in the image pickup unit disposing hole 410.

Finally, after drying the thermoplastic resin 90, the screw 168 is screwed into the screw hole 96*h*. As a result, the air supply/water supply nozzle 99 is fixed in the image pickup unit disposing hole 410 via the interposing member 170 by the screw 168, and the image pickup unit 92 that is adhered to the interposing member 170 is also fixed in the image pickup unit disposing hole 410 via the interposing member 170 by the screw 168.

Thus, according to the configuration illustrated in FIG. 8 to FIG. 10, an interposing member 170 is provided in a space between the air supply/water supply nozzle 99 and the image pickup unit 92 that are disposed in the image pickup unit disposing hole 410. By fixing the interposing member 170 with the screw 168, the image pickup unit 92 and the air supply/water supply nozzle 99 are fixed with respect to the image pickup unit disposing hole 410.

According to the above configuration, even when the screw 168 that fixes the image pickup unit 92 is not provided around the image pickup unit 92, the image pickup unit 92 can be fixed in the image pickup unit disposing hole 410 via the interposing member 170 with the screw 168 that fixes the air supply/water supply nozzle 99. Therefore, even when attempting to reduce the diameter of the distal end portion, the image pickup unit 92 can be fixed with a screw.

Further, since it is sufficient to only remove the screw 168 when replacing the image pickup unit 92, replacement of the image pickup unit 92 can be easily performed.

In side-view endoscopes, for example, when a stent is raised using the treatment instrument raiser stand 127 from the channel opening 10 of the notch portion 47*k* of the distal end portion 47, there has been a problem that illuminating light that is illuminated from the illumination lens 3 is reflected by a root portion in the vicinity of the channel opening 10 of the stent. That reflected light falls on the objective lens 20 and produces so-called halation in the observation image.

Figure 11:
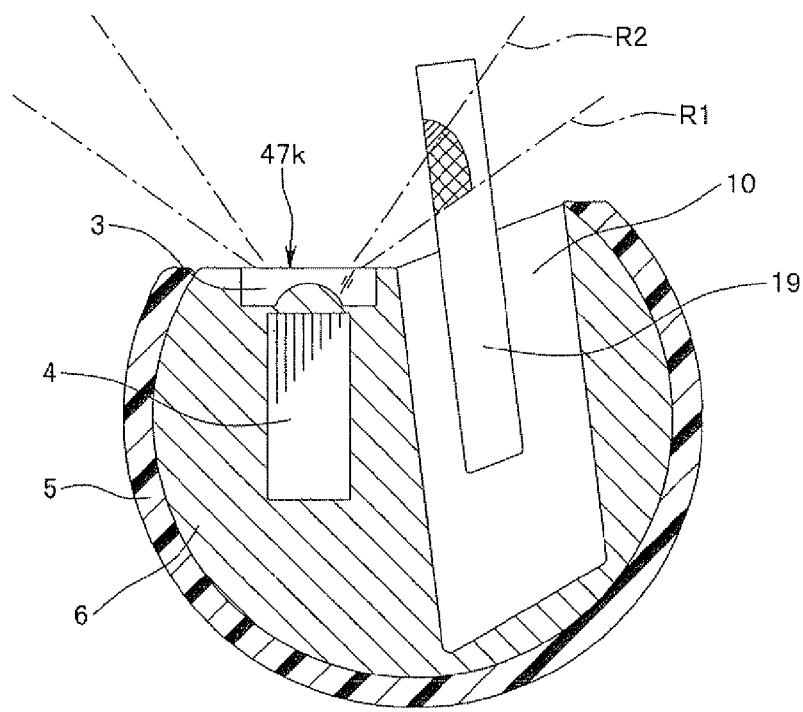
FIG. 11 is a sectional view at an illumination lens position of a distal end portion of an insertion portion of an endoscope.
Figure 12:
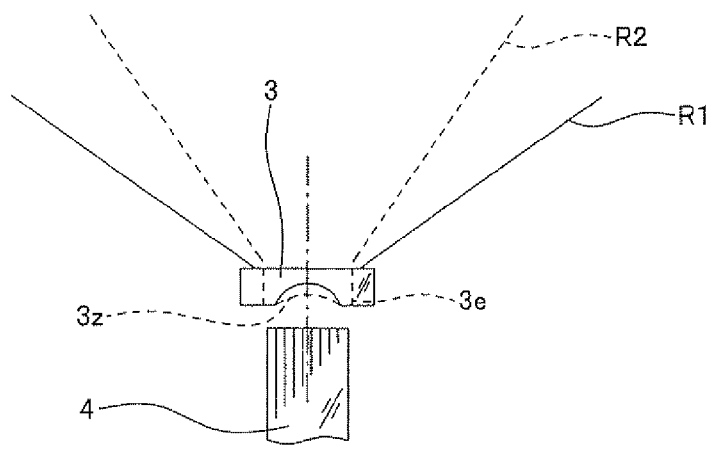
FIG. 12 is a plan view that illustrates an illumination lens and a distal end side of a light guide.
Figure 13:
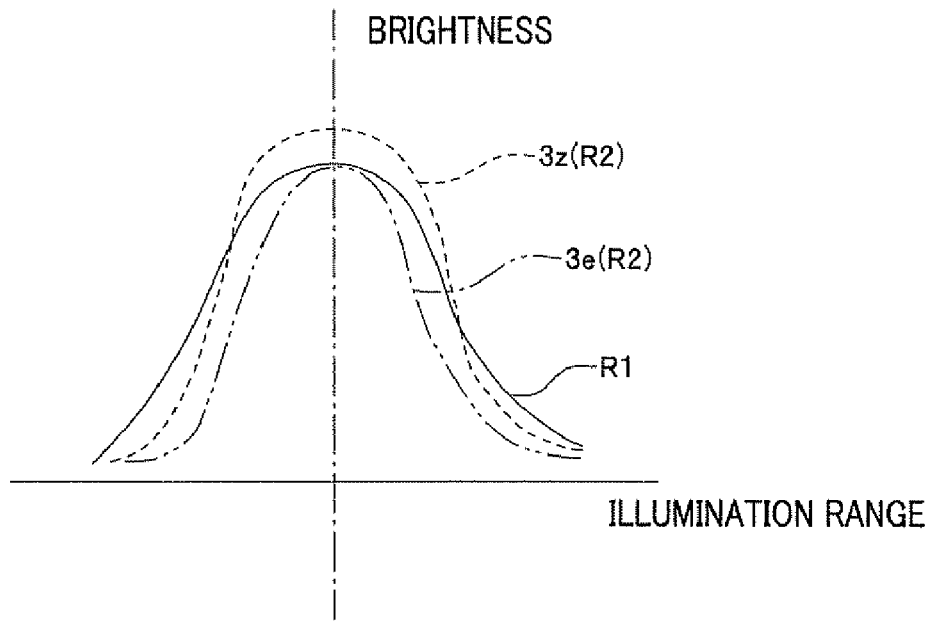
FIG. 13 is a diagram that illustrates the brightness of illuminating light with respect to an illumination range.
Figure 14:
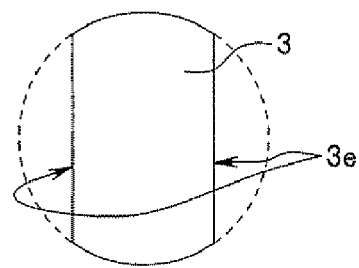
FIG. 14 is a plan view of an illumination lens that illustrates an example in which a side surface side of an illumination lens is linearly cut.

Hereunder, a configuration that prevents halation is described using FIG. 1 to FIG. 14. FIG. 11 is a sectional view at an illumination lens position of a distal end portion of an insertion portion of an endoscope, FIG. 12 is a plan view that illustrates an illumination lens and a distal end side of a light guide. FIG. 13 is a diagram that illustrates the brightness of illuminating light with respect to an illumination range. FIG. 14 is a plan view of an illumination lens that illustrates an example in which a lateral surface side of an illumination lens is linearly cut.

As shown in FIG. 11 and FIG. 12, in order to illuminate an illuminating light that is illuminated from the illumination lens 3 over a wider range, as indicated by a luminous flux R1, it is desirable to set the orientation of the illuminating light to a wider angle. However, if the orientation of the illuminating light is set to a wider angle, as described above, the illuminating light is reflected by the root portion of a stent 19 and the reflected light falls on the objective lens 20. As a result, halation is produced.

Hence, in order not to produce halation, it is preferable to set the orientation of illuminating light that is illuminated from the illumination lens 3 near the center of the illumination lens 3, as illustrated by a luminous flux R2. By setting the orientation of illuminating light near the center of the illumination lens 3, as shown in FIG. 11 and FIG. 12, it is difficult for the luminous flux R2 to be illuminated onto the root of the stent 19. It is therefore possible to prevent reflected light from the root of the stent 19 falling on the objective lens 20.

Specific means that sets the orientation of illuminating light illuminated from the illumination lens 3 near the center of the illumination lens 3, as illustrated by the luminous flux R2, is shown in FIG. 12. In FIG. 12, the R shape of a spherical surface facing the tip of the light guide 4 of the objective lens 20 including a concave lens is, as indicated by a dotted line 3z, set more loosely than a conventional R shape that is indicated by solid lines.

As a result, as indicated by the dotted line in FIG. 13, illuminating light that is illuminated from the illumination lens 3 illuminates the center range of the illumination lens 3 more brightly than the conventional illuminating light that is indicated by the solid line R1.

By utilizing this fact, since the quantity of illuminating light that illuminates the vicinity of the periphery of the illumination lens 3 is less than in the conventional configuration, it is possible to prevent illuminating light from being reflected by the root portion of the stent 19 and producing halation.

Another specific means that sets the orientation of illuminating light illuminated from the illumination lens 3 near the center of the illumination lens 3, as illustrated by the luminous flux R2, is shown in FIG. 12 and FIG. 14. In this case, it is sufficient to linearly cut, as viewed in a planar state, each side surface portion 3e facing the longitudinal direction of the channel opening 10 of the illumination lens 3 that has a circular shape when viewed in a planar state.

As a result, as illustrated by the two-dot chain line in FIG. 13, the major part of illuminating light that is illuminated from the illumination lens 3 illuminates the center range of the illumination lens 3 more than the conventional illuminating light that is indicated by the solid line R1.

By utilizing this fact, since the quantity of illuminating light that illuminates the vicinity of the periphery of the illumination lens 3 is significantly less than in the conventional configuration, it is possible to prevent illuminating light from being reflected by the root portion of the stent 19 and producing halation.

Figure 15:
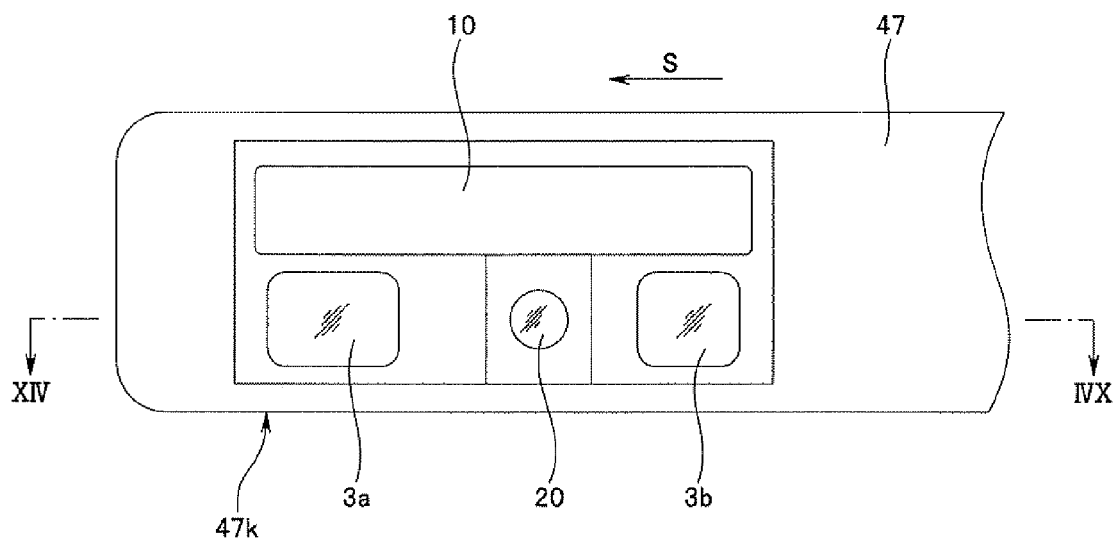
FIG. 15 is a plan view that illustrates an example in which two illumination lenses are provided in a notch portion of a distal end portion of an insertion portion of an endoscope.
Figure 16:
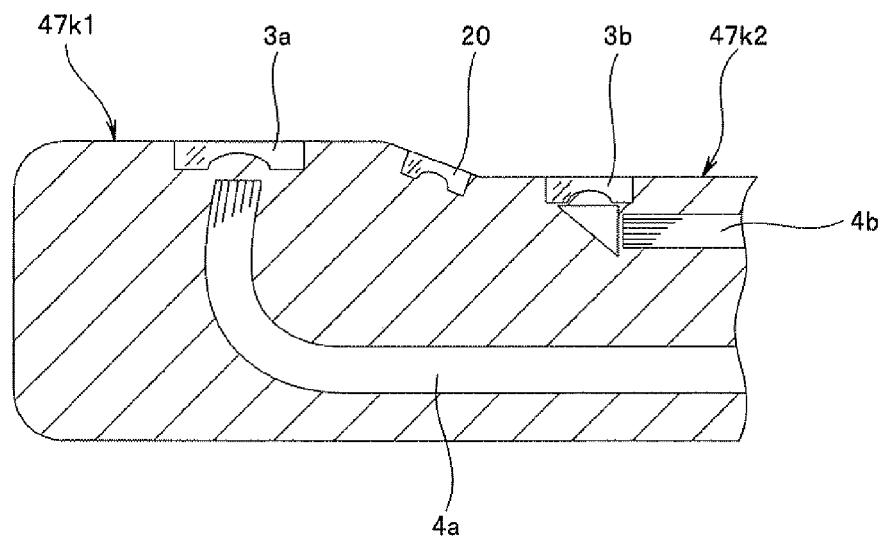
FIG. 16 is a schematic sectional view of a distal end portion along a line XIV-XIV shown in FIG. 15.

Another configuration for preventing halation is described hereunder using FIG. 15 and FIG. 16. FIG. 15 is a plan view that illustrates an example in which two illumination lenses are provided in a notch portion at a distal end portion of an insertion portion of an endoscope. FIG. 16 is a schematic sectional view of a distal end portion along a line XIV-XIV shown in FIG. 15.

As shown in FIG. 15 and FIG. 16, at the notch portion 47k, two illumination lens 3a and 3b are provided so as to sandwich the objective lens 20 along the insertion direction S. By making the light amount that is illuminated from each of the illumination lenses 3a and 3b half the amount that is illuminated from the conventional single illumination lens 3 and making the orientation direction of the illuminating light differ between the illumination lens 3a and the illumination lens 3b, the illuminating light illuminated from the respective illumination lenses 3a and 3b is prevented from concentrating on and illuminating the root portion of the stent 19. It is thereby possible to prevent the occurrence of halation caused by the stent 19.

In this connection, the configuration need not be one in which the illumination lens 3a and 3b are disposed so as to sandwich the objective lens 20, as shown in FIG. 15 and FIG. 16. Instead, two illumination lens may be disposed in a first notch surface 47k1 shown in FIG. 16, or two illumination lens may be disposed in a second notch surface 47k2 shown in FIG. 16.

The invention described in the above embodiments is not limited to those embodiments, and various modifications can be made in a wide range to the foregoing embodiments at an implementation stage without departing from the spirit and scope of the invention. It is to be understood that inventions at various stages of each embodiment are included in the embodiments, and various inventions can be extracted by appropriately combining a plurality of the constituent elements that are disclosed in the embodiments.

For example, even when several of the constituent elements are eliminated from the total constituent elements disclosed in the embodiments, in a case in which it is possible to solve a problem described in the section regarding problems to be solved by the invention, and an advantage described with respect to the advantages of the invention can be obtained, the configuration from which the constituent elements are eliminated can be extracted as an invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A side-view endoscope comprising:
    an objective lens that observes a subject is provided in at least one part of an outer peripheral surface of a distal end portion on a distal end side in an insertion direction of an insertion portion;
    a distal end main body portion provided in the distal end portion of the insertion portion;
    a disposing hole having a first space that is formed in the distal end main body portion along the insertion direction and that opens as a first opening at a rear end in the insertion direction of the distal end main body portion, and a second space that opens as a second opening in the outer peripheral surface in which the objective lens is provided of the distal end portion and which intersects in a different direction to the insertion direction with the first space; and
    an image pickup unit that has the objective lens and is provided inside the disposing hole so that the objective lens faces the second opening, and that has a shape formed along a part of the first space and the second space, wherein the image pickup unit comprises:
        an objective lens group having the objective lens, that is disposed in the second space; and objective lens frame that retains the objective lens group;
        an image pickup device that picks up images of the subject and that is provided on a light emitting side of the objective lens group which is an opposite side to the second opening of the second space;
a device frame that retains the image pickup device and is fitted on an outer circumference of an end portion of the objective lens frame on the light emitting side; and
an image pickup unit retaining frame that is disposed in the second space and the first space and is fitted on an outer circumference of an end portion of the device frame on the light emitting side and that retains the device frame, wherein:
at an intersecting region between the first space and the second space, the image pickup unit is fixed in the disposing hole by a fixing member that is inserted into the distal end main body portion through an insertion hole formed in the distal end main body portion, and
the intersecting region is located on the light emitting side with respect to the image pickup unit; and
the image pickup unit is fixed inside the disposing hole by a tip of the fixing member contacting against a contact site of the image pickup unit located in the second space from an end portion of the image pickup unit on the light emitting side and pushing up the contact site to the second opening side.

2. The endoscope according to claim 1, wherein:
the tip of the fixing member contacts against the image pickup unit retaining frame and pushes up the image pickup unit retaining frame to the second opening side to thereby push up the image pickup device that is retained in the device frame and the objective lens group that is retained in the objective lens frame to the second opening side and cause at least one part of the image pickup unit to contact against a positioning portion of the distal end main body portion that is located in the second space.

3. The endoscope according to claim 2, wherein:
a first inclined portion that is oriented to the second opening side is formed in the tip of the fixing member, and
a second inclined portion having a face that abuts against a face of the first inclined portion is formed at a site of the image pickup unit retaining frame against which the tip of the fixing member contacts.

4. The endoscope according to claim 2, wherein:
the insertion hole in the distal end main body portion is formed on an axis that inclines at a set angle to the second opening side with respect to the insertion direction and a direction perpendicular to the insertion direction, and
a third inclined portion having a face that abuts against a face of the tip which is flat of the fixing member is formed at a site of the image pickup unit retaining frame against which the tip of the fixing member contacts.

5. A side-view endoscope comprising:
an objective lens that observes a subject is provided in at least one part of an outer peripheral surface of a distal end portion on a distal end side in an insertion direction of an insertion portion;
a distal end main body portion provided in the distal end portion of the insertion portion;
a disposing hole having a first space that is formed in the distal end main body portion along the insertion direction and that opens as a first opening at a rear end in the insertion direction of the distal end main body portion, and a second space that opens as a second opening in the outer peripheral surface in which the objective lens is provided of the distal end portion and which intersects in a different direction to the insertion direction with the first space; and
an image pickup unit that has the objective lens and is provided inside the disposing hole so that the objective lens faces the second opening, and that has a shape formed along a part of the first space and the second space;

wherein, at an intersecting region between the first space and the second space, the image pickup unit is fixed in the disposing hole by a fixing member that is inserted into the distal end main body portion through an insertion hole formed in the distal end main body portion, and
wherein: at a position further on a light emitting side of the objective lens group included in the image pickup unit which is an opposite side to the second opening, than the image pickup unit in the first space are provided a light guide that supplies an illuminating light to an illumination lens that faces a third opening that is formed at a different position to the second opening in the outer peripheral surface of the distal end portion, and a light guide cover that retains the light guide and freely contacts against an end portion of the image pickup unit on the light emitting side, with the intersecting region being located at the light guide cover; and
by a tip of the fixing member contacting against the light guide cover and pushing up the light guide cover to the second opening side, the fixing member pushes up the image pickup unit to the second opening side and causes at least one part of the image pickup unit to contact against a positioning portion of the distal end main body portion located in the second space to thereby fix the image pickup unit in the disposing hole.

6. A side-view endoscope comprising:
an objective lens that observes a subject is provided in at least one part of an outer peripheral surface of a distal end portion on a distal end side in an insertion direction of an insertion portion:
a distal end main body portion provided in the distal end portion of the insertion portion:
a disposing hole having a first space that is formed in the distal end main body portion along the insertion direction and that opens as a first opening at a rear end in the insertion direction of the distal end main body portion, and a second space that opens as a second opening in the outer peripheral surface in which the objective lens is provided of the distal end portion and which intersects in a different direction to the insertion direction with the first space; and
an image pickup unit that has the objective lens and is provided inside the disposing hole so that the objective lens faces the second opening, and that has a shape formed along a part of the first space and the second space;

wherein:
at an intersecting region between the first space and the second space, the image pickup unit is fixed in the disposing hole by a fixing member that is inserted into the distal end main body portion through an insertion hole formed in the distal end main body portion, the image pickup unit comprises:
an objective lens group having the objective lens, that is disposed in the second space: an objective lens frame that retains the objective lens group;
an image pickup device that picks up images of the subject and that is provided on a light emitting side of the objective lens group which is an opposite side to the second opening of the second space;

a device frame that retains the image pickup device and is fitted on an outer circumference of an end portion of the objective lens frame on the light emitting side; and an image pickup unit retaining frame that is disposed in the second space and the first space and is fitted on an outer circumference of an end portion of the device frame on the light emitting side and that retains the device frame, at a position further on the light emitting side than the image pickup unit in the first space are provided a light guide that supplies an illuminating light to an illumination lens that faces a third opening that is formed at a different position to the second opening in the outer peripheral surface of the distal end portion, and a light guide cover that retains the light guide and freely contacts against an end portion of the image pickup unit on the light emitting side, with the intersecting region being located at the light guide cover; and by a tip of the fixing member contacting against the light guide cover and pushing up the light guide cover to the second opening side, the fixing member pushes up the image pickup unit to the second opening side and causes at least one part of the image pickup unit to contact against a positioning portion of the distal end main body portion located in the second space to thereby fix the image pickup unit in the disposing hole.

7. The endoscope according to claim 5, wherein:
a fourth inclined portion that is oriented towards the second opening side is formed in the tip of the fixing member, and
a fifth inclined portion having a face that abuts against a face of the fourth inclined portion is formed at a site of the light guide cover against which the tip of the fixing member contacts.

8. The endoscope according to claim 6, wherein:
a fourth inclined portion that is oriented towards the second opening side is formed in the tip of the fixing member, and
a fifth inclined portion having a face that abuts against a face of the fourth inclined portion is formed at a site of the light guide cover against which the tip of the fixing member contacts.

9. The endoscope according to claim 1, wherein the fixing member comprises a screw.

10. An endoscope apparatus comprising:
a side-view endoscope in which an objective lens that observes a subject is provided in at least one part of an outer peripheral surface of a distal end portion on a distal end side in an insertion direction of an insertion portion;
a distal end main body portion provided in the distal end portion of the insertion portion;
a disposing hole having a first space that is formed in the distal end main body portion along the insertion direction and that opens as a first opening at a rear end in the insertion direction of the distal end main body portion, and a second space that opens as a second opening in the outer peripheral surface in which the objective lens is provided of the distal end portion and which intersects in a different direction to the insertion direction with the first space;
an image pickup unit that has the objective lens and is provided inside the disposing hole so that the objective lens faces the second opening, and that has a shape formed along a part of the first space and the second space; and a fixing member that is inserted into the distal end main body portion through an insertion hole formed in the distal end main body portion and that fixes the image pickup unit inside the disposing hole at an intersecting region between the first space and the second space, wherein:
the image pickup unit comprises:
an objective lens group having the objective lens, that is disposed in the second space;
an objective lens frame that retains the objective lens group;
an image pickup device that picks up images of the subject and that is provided on a light emitting side of the objective lens group which is an opposite side to the second opening of the second space;
a device frame that retains the image pickup device and is fitted on an outer circumference of an end portion of the objective lens frame on the light emitting side; and
an image pickup unit retaining frame that is disposed in the second space and the first space and is fitted on an outer circumference of an end portion of the device frame on the light emitting side and that retains the device frame, and
the intersecting region is located on the light emitting side with respect to the image pickup unit; and
the image pickup unit is fixed inside the disposing hole by a tip of the fixing member contacting against a site of the image pickup unit located in the second space from the light emitting side in the image pickup unit and pushing up the contact site to the second opening side.

11. The endoscope apparatus according to claim 10, wherein:
the tip of the fixing member contacts against the image pickup unit retaining frame and pushes up the image pickup unit retaining frame to the second opening side to thereby push up the image pickup device that is retained in the device frame and the objective lens group that is retained in the objective lens frame to the second opening side and cause at least one part of the image pickup unit to contact against a positioning portion of the distal end main body portion that is located in the second space.

12. The endoscope apparatus according to claim 11, wherein:
a first inclined portion that is oriented to the second opening side is formed in the tip of the fixing member, and
a second inclined portion having a face that abuts against a face of the first inclined portion is formed at a site of the image pickup unit retaining frame against which the tip of the fixing member contacts.

13. The endoscope apparatus according to claim 11, wherein:
the insertion hole in the distal end main body portion is formed on an axis that inclines at a set angle to the second opening side with respect to the insertion direction and a direction perpendicular to the insertion direction, and
a third inclined portion having a face that abuts against a face of the tip which is flat of the fixing member is formed at a site of the image pickup unit retaining frame against which the tip of the fixing member contacts.

14. An endoscope apparatus, comprising
a side-view endoscope in which an objective lens that observes a subject is provided in at least one part of an outer peripheral surface of a distal end portion on a distal end side in an insertion direction of an insertion portion;

a distal end main body portion provided in the distal end portion of the insertion portion;

a disposing hole having a first space that is formed in the distal end main body portion along the insertion direction and that opens as a first opening at a rear end in the insertion direction of the distal end main body portion, and a second space that opens as a second opening in the outer peripheral surface in which the objective lens is provided of the distal end portion and which intersects in a different direction to the insertion direction with the first space;

an image pickup unit that has the objective lens and is provided inside the disposing hole so that the objective lens faces the second opening, and that has a shape formed along a part of the first space and the second space; and a fixing member that is inserted into the distal end main body portion through an insertion hole formed in the distal end main body portion and that fixes the image pickup unit inside the disposing hole at an intersecting region between the first space and the second space, wherein:

at a position further on a light emitting side of the objective lens group included in the image pickup unit which is an opposite side to the second opening, than the image pickup unit in the first space are provided a light guide that supplies an illuminating light to an illumination lens that faces a third opening that is formed at a different position to the second opening in the outer peripheral surface of the distal end portion, and a light guide cover that retains the light guide and freely contacts against an end portion of the image pickup unit on the light emitting side, with the intersecting region being located at the light guide cover; and by a tip of the fixing member contacting against the light guide cover and pushing up the light guide cover to the second opening side, the fixing member pushes up the image pickup unit to the second opening side and causes at least one part of the image pickup unit to contact against a positioning portion of the distal end main body portion located in the second space to thereby fix the image pickup unit in the disposing hole.

15. The endoscope apparatus according to claim 14, wherein:

a fourth inclined portion that is oriented towards the second opening side is formed in the tip of the fixing member, and a fifth inclined portion having a face that abuts against a face of the fourth inclined portion is formed at a site of the light guide cover against which the tip of the fixing member contacts.

16. The endoscope apparatus according to claim 10, wherein the fixing member comprises a screw.

* * * * *